United States Patent
Aferzon et al.

(10) Patent No.: US 12,231,612 B2
(45) Date of Patent: Feb. 18, 2025

(54) STEREOSCOPIC CAMERA ADAPTER FOR ENABLING DOWN-HOLE DATA CAPTURE AND TRANSMISSION

(71) Applicant: Mantis Health, Inc., Stamford, CT (US)

(72) Inventors: Joshua Aferzon, Avon, CT (US); Lee Nicholson, Unionville (CA)

(73) Assignee: Mantis Health, Inc., Stamford, CT (US)

( * ) Notice: Subject to any disclaimer, the term of this patent is extended or adjusted under 35 U.S.C. 154(b) by 0 days.

(21) Appl. No.: 18/129,678

(22) Filed: Mar. 31, 2023

(65) Prior Publication Data
US 2023/0319254 A1  Oct. 5, 2023

Related U.S. Application Data

(60) Provisional application No. 63/326,831, filed on Apr. 2, 2022.

(51) Int. Cl.
*H04N 13/239* (2018.01)
*A61B 17/02* (2006.01)
*H04N 7/18* (2006.01)

(52) U.S. Cl.
CPC .......... *H04N 13/239* (2018.05); *A61B 17/02* (2013.01); *H04N 7/183* (2013.01)

(58) Field of Classification Search
CPC ....... H04N 13/239; H04N 7/183; A61B 17/02
See application file for complete search history.

(56) References Cited

U.S. PATENT DOCUMENTS

| | | | | |
|---|---|---|---|---|
| 9,438,773 | B2* | 9/2016 | Howes | A61B 3/135 |
| 2012/0253121 | A1* | 10/2012 | Kitano | A61B 1/0623 |
| | | | | 600/109 |
| 2013/0281791 | A1* | 10/2013 | Aferzon | A61B 1/06 |
| | | | | 600/245 |
| 2014/0378843 | A1* | 12/2014 | Valdes | A61B 1/063 |
| | | | | 600/476 |
| 2015/0018622 | A1* | 1/2015 | Tesar | A61B 90/20 |
| | | | | 600/202 |
| 2015/0141755 | A1* | 5/2015 | Tesar | G02B 21/362 |
| | | | | 600/109 |
| 2015/0157387 | A1* | 6/2015 | OuYang | A61B 1/3132 |
| | | | | 606/34 |
| 2015/0297311 | A1* | 10/2015 | Tesar | G02B 21/0012 |
| | | | | 600/109 |
| 2018/0116489 | A1* | 5/2018 | Aferzon | A61B 1/0607 |
| 2019/0289284 | A1* | 9/2019 | Smith | A61B 1/00193 |

* cited by examiner

*Primary Examiner* — Kathleen V Nguyen
(74) *Attorney, Agent, or Firm* — Hoffmann & Baron, LLP

(57) ABSTRACT

A stereoscopic adapter for enabling down-hole data capture and transmission, the stereoscopic adapter including, stereo camera module including at least two cameras, at least two camera lenses, a prism, and a tubular retractor.

20 Claims, 19 Drawing Sheets

STEREOSCOPIC CAMERA ADAPTER FOR ENABLING DOWN-HOLE DATA CAPTURE AND TRANSMISSION

CROSS-REFERENCE TO RELATED APPLICATIONS

This application claims the benefit of priority of U.S. Provisional Patent Application Ser. No. 63/326,831, filed on Apr. 2, 2022, and titled "STEREOSCOPIC CAMERA ADAPTER FOR ENABLING DOWN-HOLE DATA CAPTURE AND TRANSMISSION," which is incorporated by reference herein in its entirety.

FIELD OF THE INVENTION

The present invention generally relates to the field of stereoscopic camera adapters. In particular, the present invention is directed to a stereoscopic adapter for enabling down-hole data capture and transmission.

BACKGROUND

Minimally invasive surgical techniques utilize a variety of retractors to perform medical procedures through small incisions in a patient. However, the reduction of the opening into the patient greatly reduces a surgeon's visibility through the portal into the surgical field. There is a need for a device that enables surgeons to increase visibility through the portal into the surgical field.

SUMMARY OF THE DISCLOSURE

In an aspect, a stereoscopic adapter for enabling down-hole data capture and transmission, the stereoscopic adapter including, stereo camera module including at least two cameras, at least two camera lenses, a prism, and a tubular retractor.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
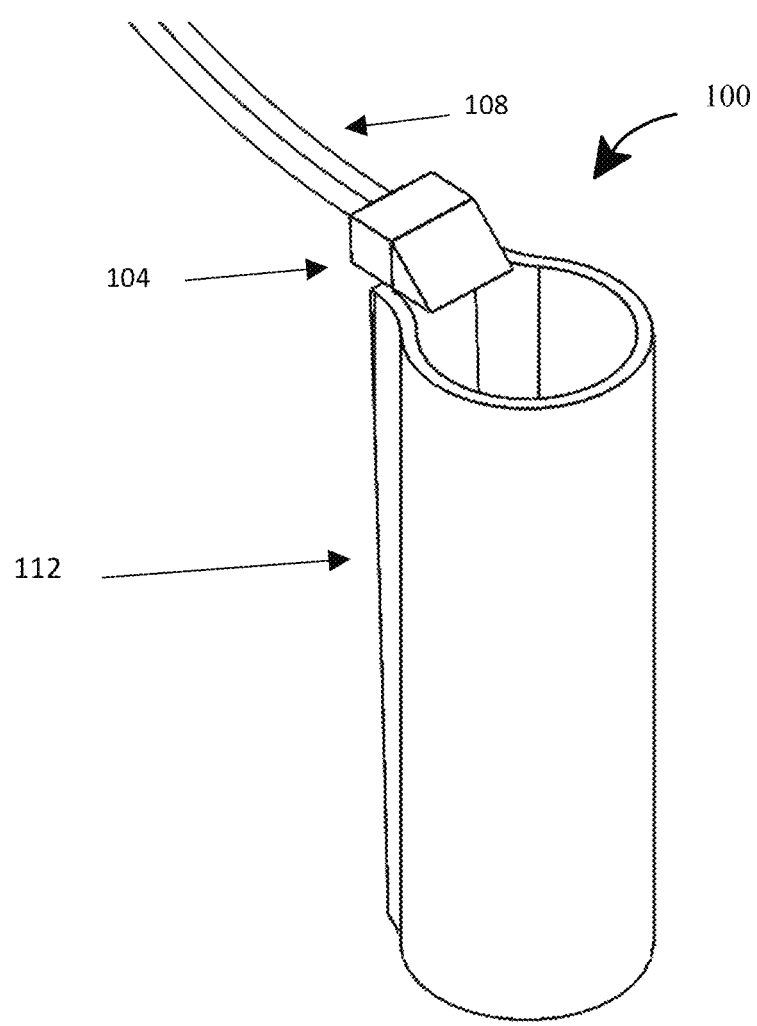
FIG. 1 illustrates a perspective view of a stereoscopic camera adapter connected to a tubular retractor for enabling stereoscopic down-hole data capture and transmission.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

The present disclosure relates to a stereoscopic camera adapter. More particularly, the present disclosure relates to a stereoscopic adapter for enabling down-hole data capture and transmission. The stereoscopic camera adapter may include a stereo camera module, a mirrored prism, an outer casing, and plurality of data cables. The stereo camera module may include two cameras, two camera lenses, and a stereo camera housing. The stereoscopic camera adapter may be attached to a tubular retractor such that the adapter is low-profile relative to the central aperture of the tubular retractor for providing unobstructed access. The tubular retractor may include a wall recess that extends beyond the circular perimeter of the retractor for the purposes of accommodating the cameras. The mirrored prism may be positioned so that is located within the tubular retractor aperture and includes a mirrored wall that reflects incoming light from the interior region, base and below the tubular retractor into the stereoscopic camera adapter.

Exemplary embodiments illustrating aspects of the present disclosure are described below in the context of several specific examples. Apparatuses and methods as disclosed herein may be used in a system for enabling maneuverable stereoscopic field of view as disclosed in in U.S. patent application Ser. No. 18/129,601, filed on Mar. 31, 2023, and entitled "FLEXIBLE AND TENSIONED CAMERA APPARATUS WITH ELECTRONIC MODULE SYSTEM FOR ENABLING MANEUVERABLE STEREOSCOPIC FIELD OF VIEW". A "stereoscopic field of view," as used herein, is the viewing of an object as three-dimensional. Enabling a stereoscopic field of view may include the "stereoscopy," which as used herein, is a technique for creating or enhancing depth perception in an image by means of stereopsis for binocular vision.

System may include a camera configured to capture image data as described further below. System may include an electronics module including at least a processor and a memory communicatively connected to the at least a processor, wherein the memory contains instructions configuring the at least a processor to receive the image data from the camera, process the image data; and transmit stereoscopic video data to one or more head-worn visualization systems as described further below. In some embodiments, a system for enabling maneuverable stereoscopic field of view may include a machine vision system that includes a camera as described through this disclosure. A machine vision system may use images from at least camera, to make a determination about a scene, space, and/or object. For example, in some cases a machine vision system may be used for world modeling or registration of objects within a space. In some cases, registration may include image processing, such as without limitation object recognition, feature detection, edge/corner detection, and the like. Non-limiting example of feature detection may include scale invariant feature transform (SIFT), Canny edge detection, Shi Tomasi corner detection, and the like. In some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and $\phi$ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level.

Referring now to FIG. 1, an exemplary perspective view of a stereoscopic camera adapter 100 connected to a tubular retractor 112 for enabling stereoscopic down-hole data capture and transmission is illustrated. Stereoscopic camera adapter 100 includes an outer casing 104. In some embodiments, stereoscopic camera adapter 100 may include a plurality of data cables 108 communicatively connected to an electronics module. A "data cable," as used herein, is a media that allows baseband transmissions from a transmitter to a receiver. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure. Stereoscopic camera adapter 100 may be a stereoscopic camera adaptable in size to a plurality of medical devices. A "stereoscopic camera," as used herein, is s a type of camera with two or more lenses with a separate image sensors. Stereoscopic camera adapter 100 may include a 3D camera, such as a 4K imaging device that enables the perception of depth in images to replicate three dimensions as experienced through human binocular vision. Some 3D cameras may use two or more lenses to record multiple points of view, while others may use a single lens that shifts its position. Types of 3D cameras may include a stereo camera, 3D scanner, range camera, structed light camera or an imaging device capable of stereo vison, Time-of-flight (ToF), 3D scanning, laser triangulation, and the like. In some embodiments, stereoscopic camera adapter 100 may include a first camera, a second camera, image signal processor boards, and/or a light source housed within outer casing 104. First camera and second camera may include any type of cameras as disclosed. An "image signal processor board," as used use herein, is an electronic circuit board configured to process image data. "Image data," as used herein, is data depicting an object of interest. For example, image data may include pictures or video captured by first camera and second camera. Image data may include a two-dimensional or three-dimensional still image moving image, still frame, and the like. Image signal processor boards may process image data captured by first camera and second camera, such as debayering, color correction, hue, saturation, brightness, white balance, compression to various codecs including but not limited to YUV, JPEG, MPEG2, AVC/H.264, VP8, and other image signal processing functions, and then format the image data to be sent via the image data cables 108. In a first embodiment, first camera and second camera may be attached to their own respective image signal processor boards via a wire or direct electrical connection. In another embodiment, first camera and second camera may be attached to a common image signal processor board. First camera may include a first camera lens, and the second camera may include a second camera lens, for the purposes of magnifying and focusing the incoming images onto the pixels of the cameras. Camera lens may include a parfocal lens, varifocal lens, telescopic lens, superzoom lens, wide-angle zoom lens, and the like. A "parfocal lens," for the purposes of this disclosure, is a lens that is configured to say in focus when the focal length is changed. A "varifocal lens," for the purposes of this disclosure, is a lens with a variable focal length in which focus changes as focal length is changed. Lenses of first camera and second camera may be interchangeable. First camera lens and second camera lens may be formatted to accept light frequencies from a visible spectrum, infrared spectrum, or other spectrums. Light source may include of an LED, Xenon-bulb circuit, or fiber optic cables and receive power from light source power cable connected to camera adapter 100 and to the electronics module.

Figure 2:
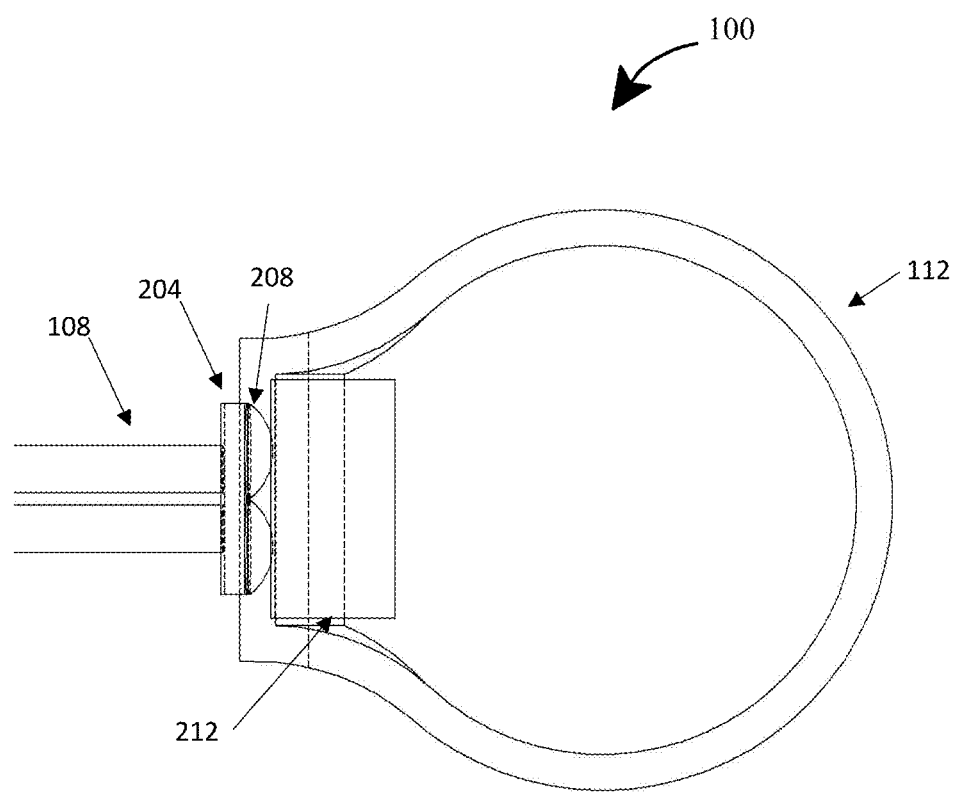
FIG. 2 illustrates a top view of a stereoscopic camera adapter, including two cameras, two lenses, a prism, and an outer casing, and data cables, connected to a tubular retractor, where the stereoscopic camera adapter occupies a minimal region of the tubular retractor and does not block the central channel.

Referring now to FIG. 2, an exemplary a top view of stereoscopic camera adapter 100, including two cameras 204, two lenses 208, a prism 212, and data cables 108, connected to a tubular retractor 112, wherein the stereoscopic camera adapter 100 occupies a minimal region of the tubular retractor 112 and does not block the central channel is illustrated. As a non-limiting example, minimal region may be less than 35% of the cross-sectional area of retractor 112. As a non-limiting example, minimal region may be less than 25% of the cross-sectional area of retractor 112. As a non-limiting example, minimal region may be less than 15% of the cross-sectional area of retractor 112. As a non-limiting example, prism 212 may allow for the stereoscopic camera adapter to occupy a minimal region of tubular retractor by allowing cameras 204 to be located outside of tubular retractor 112 and transverse the longitudinal axis of tubular retractor 112. Prim 212 may allow for this by deflecting light rays inside of tubular retractor to cameras 204. Two cameras 204 and two lenses 208 may refer to the first and second camera and cameras lenses as described above. A "retractor," as used herein, is a surgical instrument used to separate the edges of a surgical incision or wound, or to hold away certain organs and tissues so that body parts underneath may be accessed during surgical operations. Tubular retractor 112 may include a surgical retractor with rotational stabilizing locking apparatus for providing access to a surgical cavity is disclosed U.S. Nonprovisional patent application Ser. No. 13/833,759, filed on Mar. 15, 2013, and titled "ROTATIONAL STABILIZING LOCKING MECHANISM," which is incorporated by reference herein in its entirety. For example, a surgical retractor with rotational stabilizing locking apparatus may include an outer arcuate blade having a first proximal end and an opposed first distal end. The outer arcuate blade may include a coupling aperture. An inner arcuate blade may be in sliding engagement with the outer arcuate blade. Also, the inner arcuate blade may include a first prong slot forming a first gap extending through a full thickness of the inner arcuate blade. Additionally, the inner arcuate blade may include a second proximal end, an opposed second distal end and a coupling tab configured to be disposed within the coupling aperture. The rotational stabilizing locking apparatus may include a central body having an attachment arm extending away from the outer arcuate blade and the inner arcuate blade. Also, a first interfacing prong may extend from the central body into the first prong slot.

Still referring to FIG. 2, a "prism," as used herein, is a transparent object with light refracting capabilities that separates white light into a spectrum of colors. Prism 212 may include material such as glass acrylic, fluorite, and the like. Prism 212 may include a dispersive prism which may be used to break up light into its constituent spectral colors because the refractive index of light depends on wavelength. Prism 212 may include a reflective prism which may be used to reflect light, in order to flip, invert, rotate, deviate or displace the light beam. In some embodiments, prism 212 may include a mirrored hypotenuse wall that enables reflection of incoming light into cameras 204 for stereoscopic image data capture. In some embodiments, prism 212 may be used to bend light, glares, and reflections before they enter cameras 204. Prism 212 may include a prism lens. A "prism lens," as used herein is type of lens with an unique ability to bend glare, light, and reflections before allowing these to penetrate a camera lens. Prism lenses may range from 311 mm, 24 mm, and 110 mm lenses. Prism lenses may include any type of prism as described above in a camera lenses format. Prism 212 may be attached or inserted into tubular retractor 202 at an opening of a top or bottom end of tubular retractor 202.

Figure 3A:
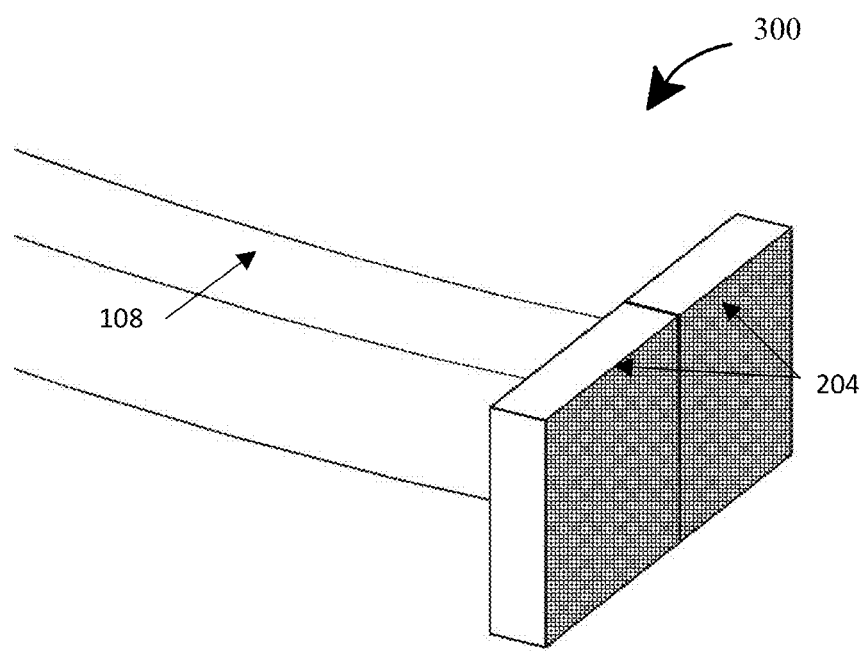
FIG. 3A illustrates a perspective view of two cameras aligned in parallel for enabling stereopsis when capturing visible light, infrared light, UV light, or other non-visible light on the electromagnetic spectrum.

Referring now to FIG. 3A, an exemplary perspective view of two cameras 204 aligned in parallel for enabling stereopsis when capturing visible light, infrared light, UV light, or other non-visible light on the electromagnetic spectrum is illustrated. Aligning camera 204 in parallel to each other may create binocular vision.

Figure 3B:
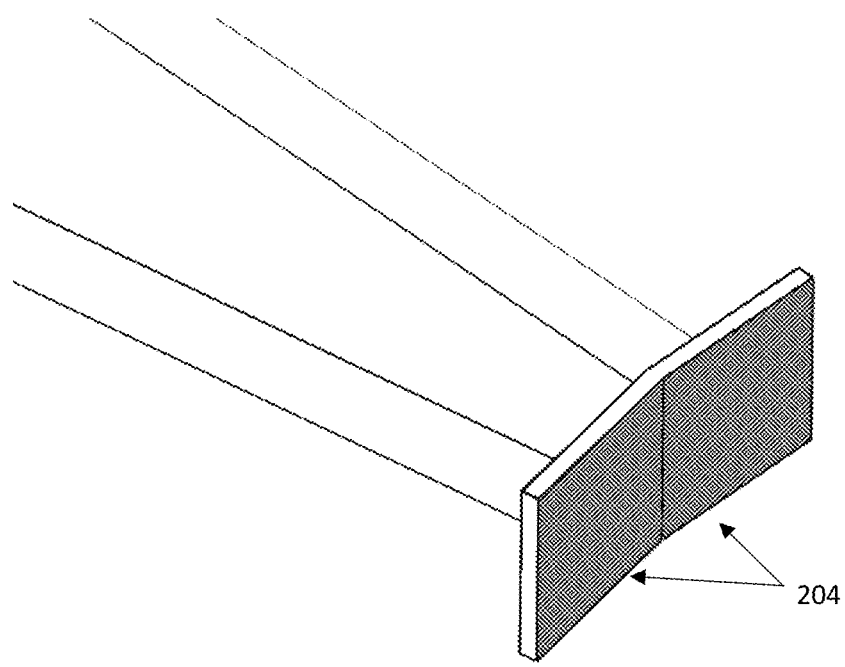
FIG. 3B illustrates a perspective view of two cameras aligned at an angle relative to one another for enabling increased parallax and stereopsis when capturing visible light, infrared light, UV light, or other non-visible light on the electromagnetic spectrum.

Referring now to FIG. 3B, an exemplary perspective view of two cameras 204 aligned at an angle relative to one another for enabling increased parallax and stereopsis when capturing visible light, infrared light, UV light, or other non-visible light on the electromagnetic spectrum is illustrated. "Parallax," as used herein, is a displacement or difference in the apparent position of an object viewed along two different lines of sight and is measured by the angle or half-angle of inclination between those two lines. "Binocular vision," as used herein, is a type of vision in which incorporating angles of vision capable of facing the same direction to perceive a single three-dimensional image of its surroundings. For example, binocular vison may relate to the left and right eye of human.

Figure 4A:
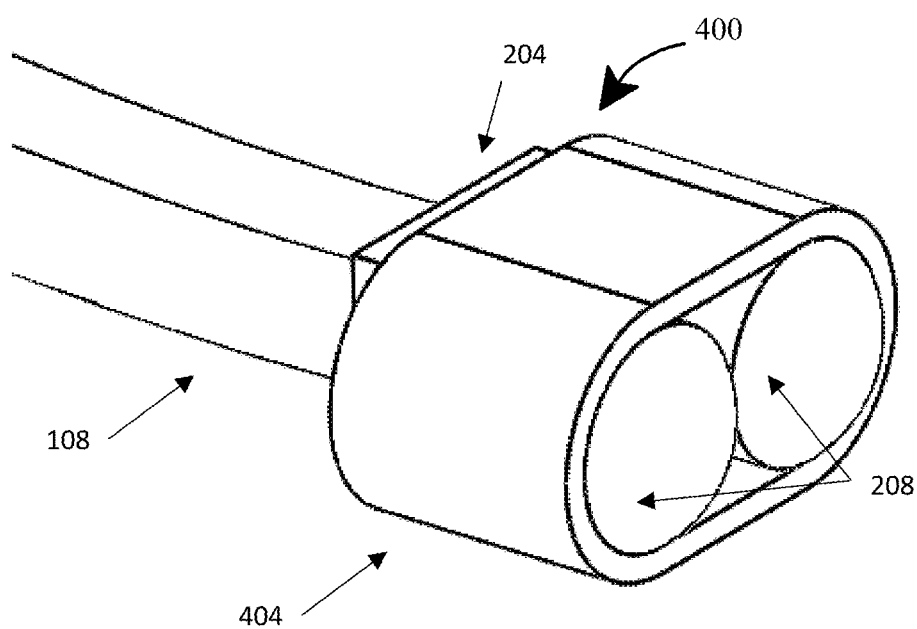
FIG. 4A illustrates a stereoscopic camera module, including cameras, lenses, data cables, and a camera adapter housing that enables stereoscopic data capture.

Referring now to FIG. 4A, an exemplary embodiment of a stereoscopic camera module 400, including cameras 204, lenses 208, data cables 108, and a camera adapter housing 404 that enables stereoscopic data capture is illustrated. Stereoscopic camera module 400 may attach to a medical device such as retractor, as described in FIG. 1. Stereoscopic camera module 400 may be used with a device configured for more invasive surgical operations. Stereoscopic camera module 400 may be connected to an electronics module in as system for enabling maneuverable stereoscopic field of view, as described above.

Figure 4B:
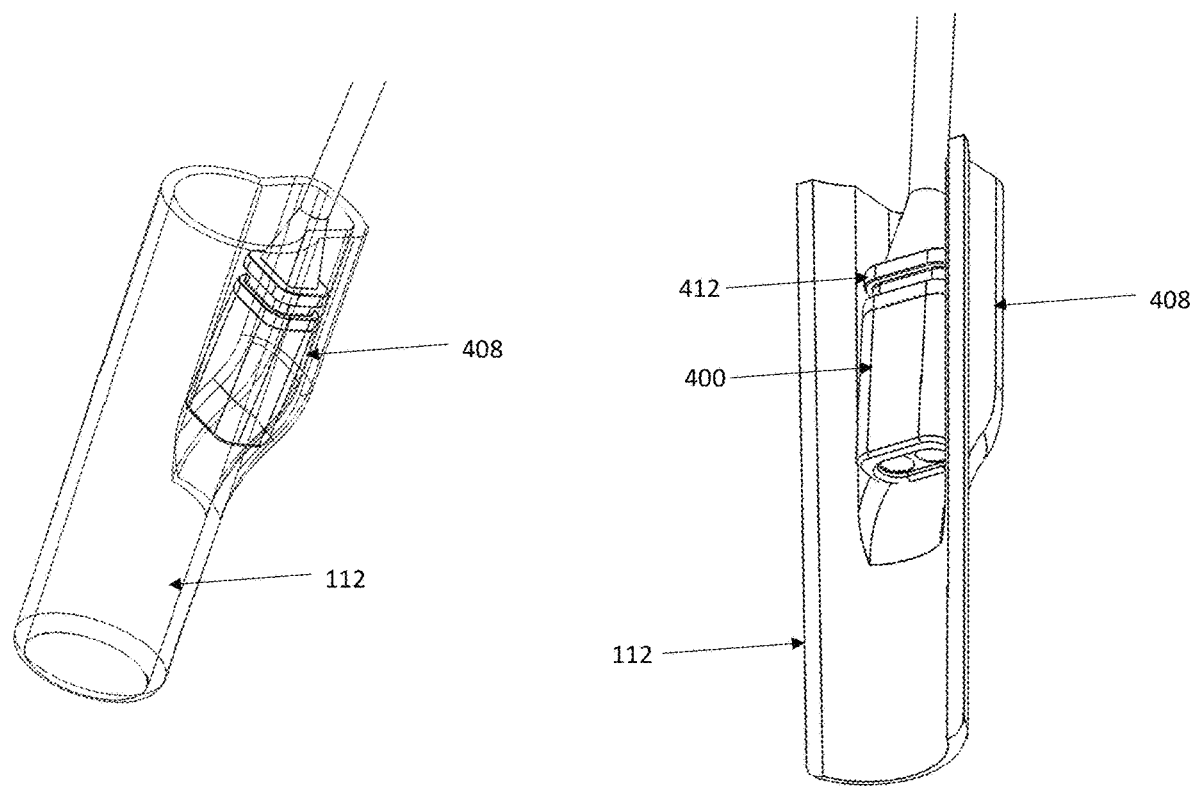
FIG. 4B illustrates cross-sectional views of a stereoscopic camera module inserted into an extended back wall cavity of a tubular retractor placed at half length of the tubular retractor.

Referring now to FIG. 4B, cross-sectional views of a stereoscopic camera module 400 inserted into an extended back wall cavity 408 of a tubular retractor 112 placed at half length of the tubular retractor 112 embodiments are illustrated. An "extended back wall cavity," as use herein, is a portion of a reactor configured to allow the insertion of an object. For example, extended back wall cavity may allow for the insertion of stereoscopic camera module 400. Extended back wall cavity 408 may be shaped to fit stereoscopic camera module 400 along the side of tubular retractor 112. Extended back wall cavity 408 may extend halfway down the length of tubular retractor 112. Additionally, in some embodiments, camera module 400 may include a cut-out feature 142 located around the perimeter of the two cameras 204 or as part of camera adapter housing 404. A "cut-out feature," is a component of a stereoscopic camera module that allows for attachment to a plurality of devices. For example cut-out feature may allow for the attachment to retractors, light cables, wedges, surgical instruments, and the like. For example, cut-out feature 412 may be shaped in a way to allow the insertion and/or fixation of a stereoscopic camera module into extended back wall cavity 408.

Figure 4C:
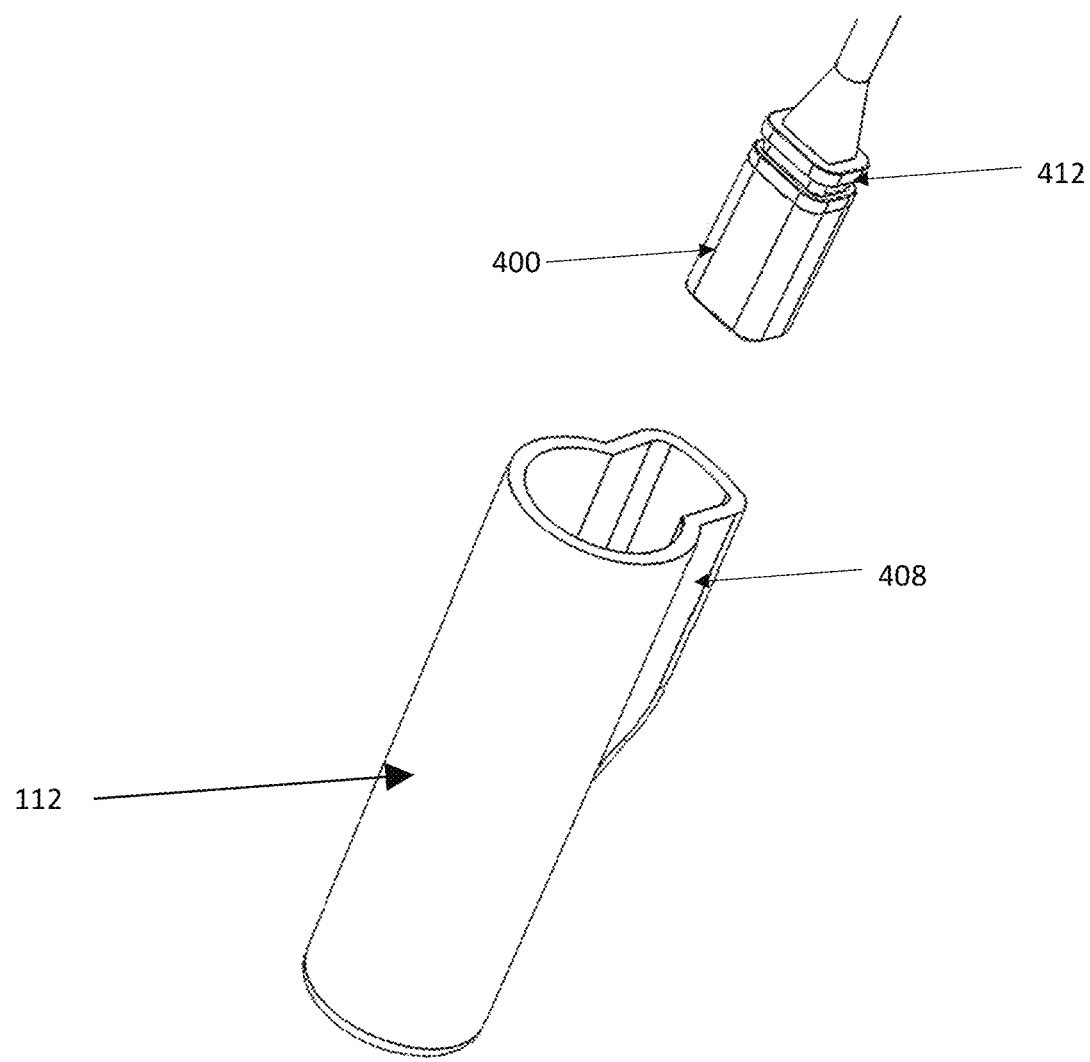
FIG. 4C illustrates a holistic view of a stereoscopic camera module and tubular retractor including an extended back wall cavity.

Referring now to FIG. 4C, a holistic view of a stereoscopic camera module 400 and tubular retractor 112 including an extended back wall cavity 408 embodiment is illustrated.

Figure 4D:
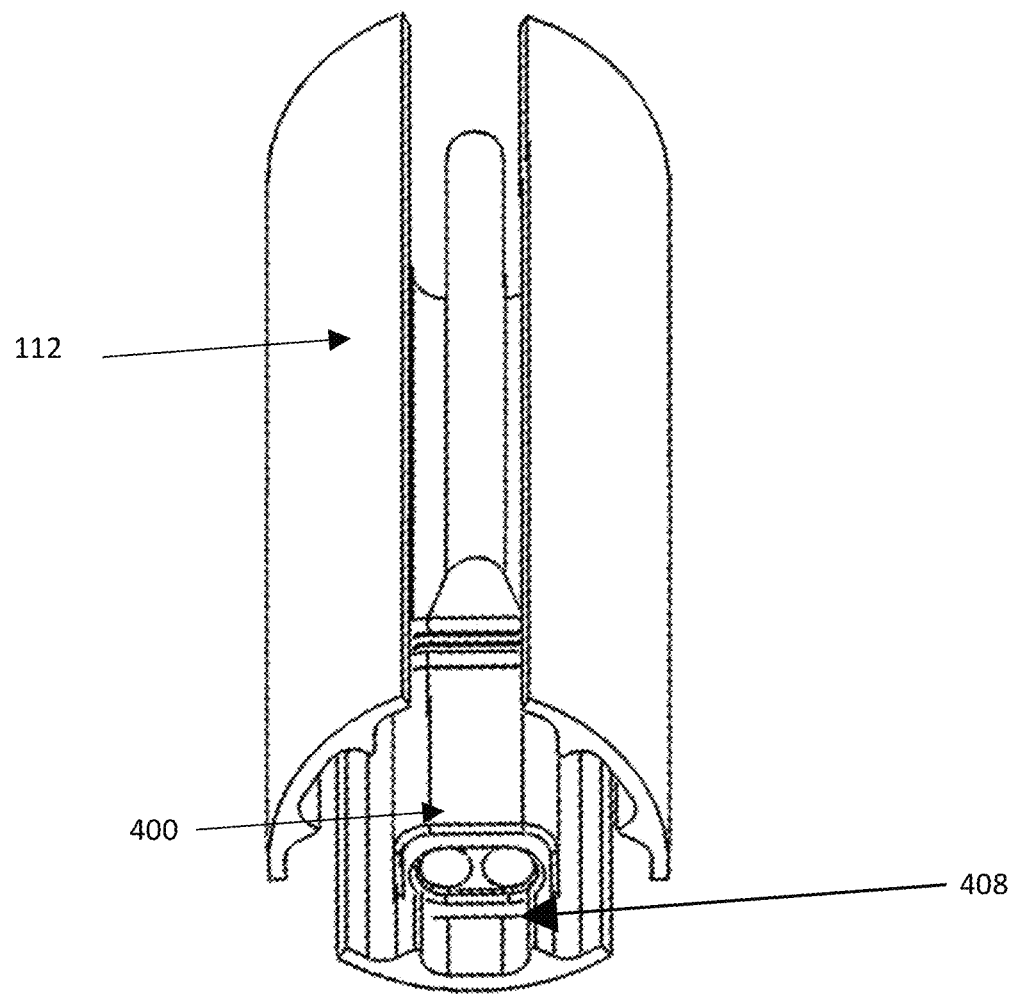
FIG. 4D illustrates a stereoscopic camera module inserted into an extended back wall cavity of a tubular retractor extending fully down the length of the tubular retractor.

Referring now to FIG. 4D, a stereoscopic camera module 400 inserted into an extended back wall cavity 408 of a tubular retractor 112 extending fully down the length of the tubular retractor 112 embodiment is illustrated. Extended back wall cavity 408 may be incorporated into any retractor as described throughout this disclosure.

Figure 5:
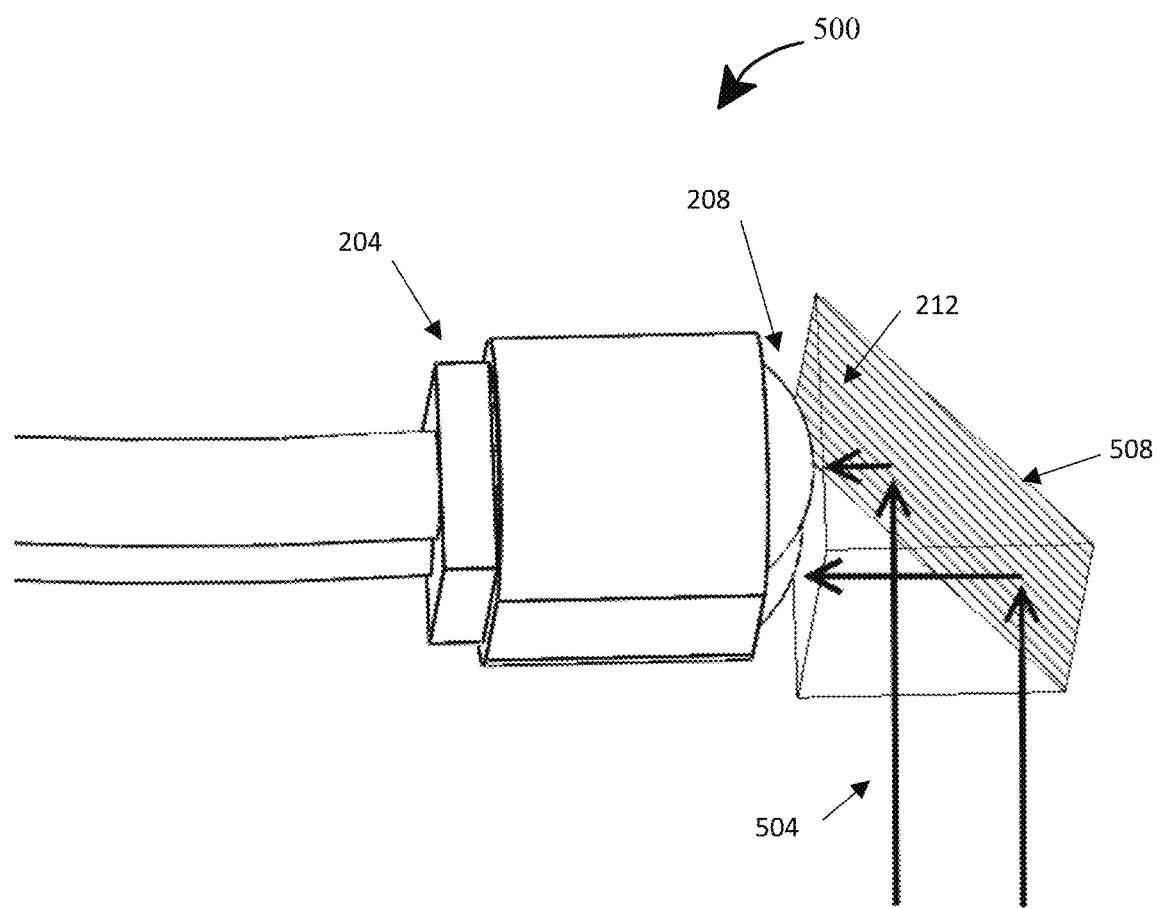
FIG. 5 illustrates a stereo camera module attached to, or placed next to, a prism, where the prism includes a mirrored hypotenuse wall that enables reflection of incoming light into the cameras for stereoscopic data capture.

Referring now to FIG. 5, an exemplary embodiment of a stereo camera module 400 attached to, or placed next to, a prism 212, where prism 212 includes a mirrored hypotenuse wall 508 that enables reflection of incoming light 504 into the cameras for stereoscopic data capture, for example and with reference, to FIG. 2 is illustrated.

Figure 6:
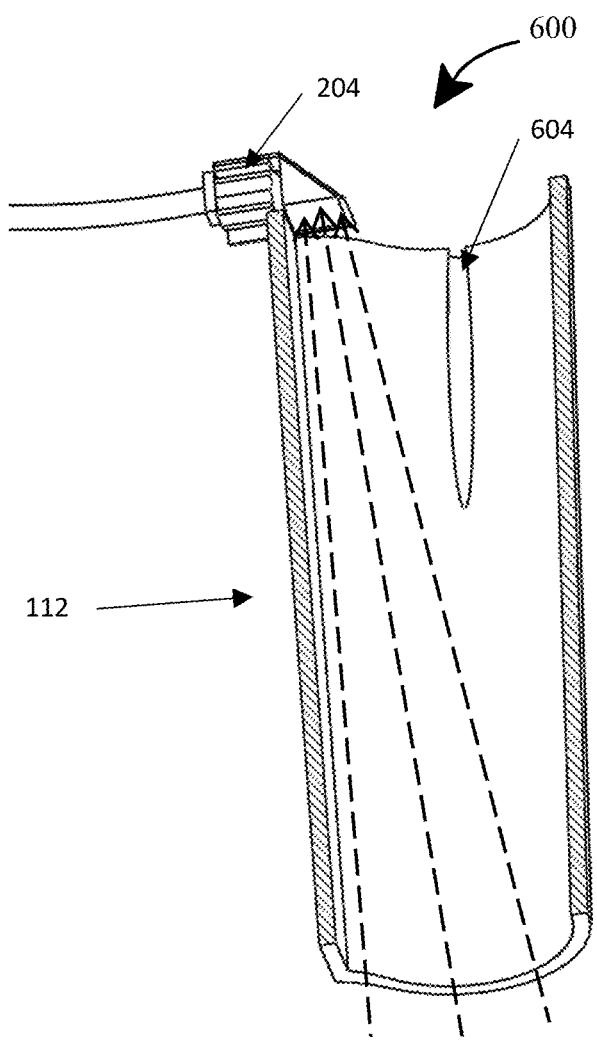
FIG. 6 illustrates a sectioned view of a stereoscopic camera adapter connected to a tubular retractor, where the prism within the stereoscopic camera adapter is angled relative to the top plane of the tubular retractor so that the entire base of, and the anatomy below, the tubular retractor is within view of the cameras.

Referring now to FIG. 6, an exemplary a sectioned view of a stereoscopic camera adapter 100 connected to a tubular retractor 112, where the prism 212 within the stereoscopic camera adapter 100 is angled relative to the top plane of the tubular retractor 112 so that the entire base of and the anatomy below the tubular retractor 112 is within view of the cameras 204 is illustrated. In some embodiments, tubular retractor 112 may include a light a light guide channel 604 as described below.

Figure 7:
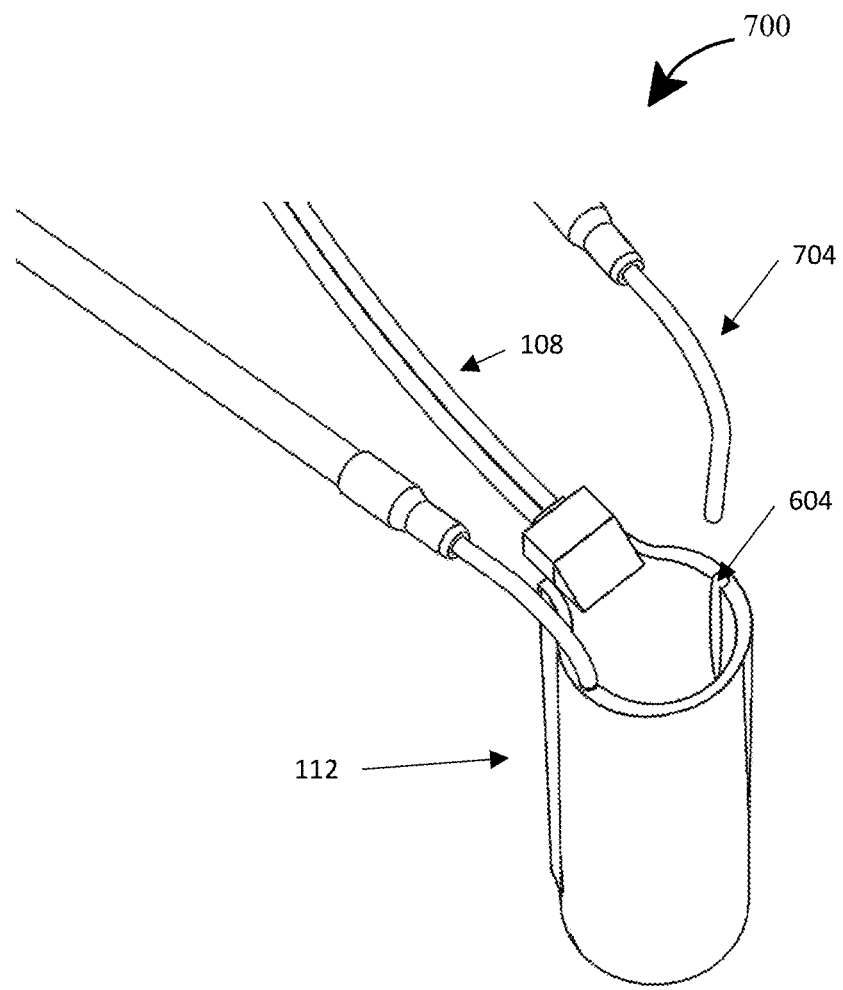
FIG. 7 illustrates a plurality of light guides being inserted into a tubular retractor via a light guide channel cut into the wall of the tubular retractor.

Referring now to FIG. 7, an exemplary diagram of a plurality of light guides 704 being inserted into a tubular retractor 112 via a light guide channel 604 cut into the wall of the tubular retractor 112 is illustrated. A 'light guide," as used herein, is a tool for transmitting light. For example, light guide 704 may include fiber-optic cable. A "fiber-optic cable," as used herein, is an assembly containing one or more optical fibers that are used to carry light. Light guide may include other forms of light device. A "light device," as use herein, is a light source. For example, a light device may be a flashlight. A "light guide channel," as used herein, is channel or tubular passageway for conveying and/or guiding supplementary instruments, such as light guides, cameras, and suction tools, into a surgical cavity. These supplementary instruments may then be anchored to one or more mounting apertures of tubular retractor 112 to prevent the wiring from blocking or obstructing the cameras 204 field of vision. Light guide channel 604 may containing light guide 704.

Figure 8:
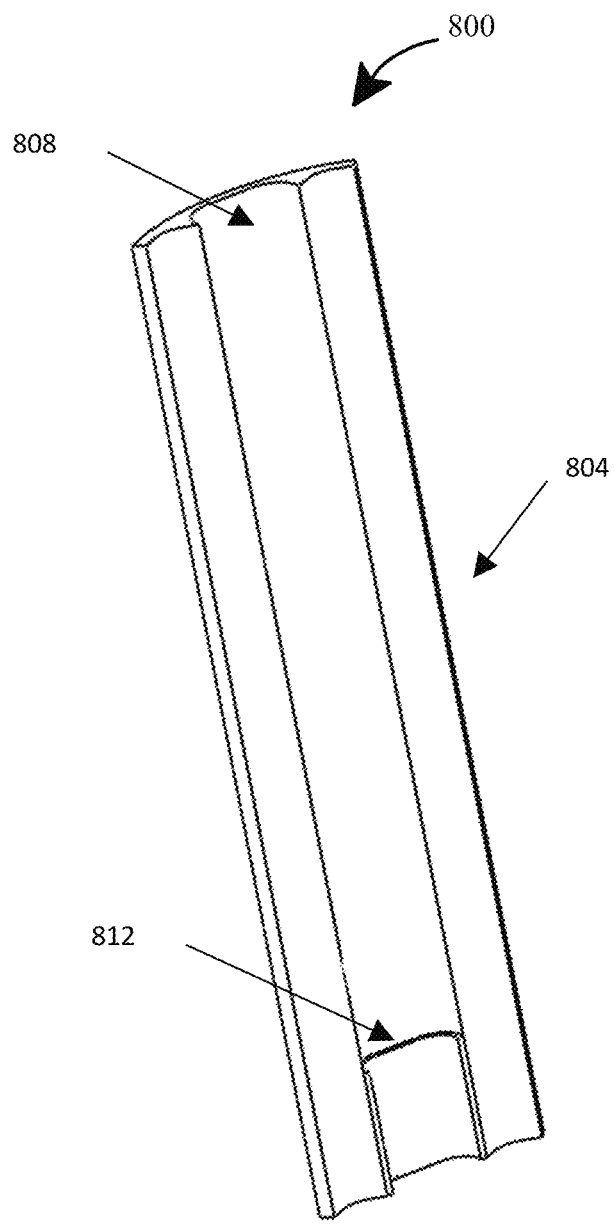
FIG. 8 illustrates a blade mechanism which includes a blade, a camera cut-out and a stopper that enables retainment of muscles or other anatomy in the body so there is unobstructed access to deeper regions.

Referring now to FIG. 8, an exemplary embodiment of a blade mechanism 800 which may include a blade 802, a camera cut-out 808 and a stopper 812 that enables retainment of muscles or other anatomy in the body so there is unobstructed access to deeper regions is illustrated. A "blade," as used herein, is a retaining device. For example, a retaining device in a retractor may a device configured to hold muscle back by force when inserted into the anatomy of a person. A blade may also include a cutting device. Blade mechanism 800 may be conical or rectangular and flat in shape. Blade mechanism 800 may be configured for a blade surgical retractor. A "blade mechanism," as used herein, a portion of a device configured to perform a blade function, A blade function may include puncturing, chopping, slicing, retaining, holding, blocking, cutting, scraping, and the like. A "blade surgical retractor," as used herein, is a retractor including a blade. For example, blade mechanism may be incorporated in or include a Richardson retractor, Deaver retractor, Harrington or "sweetheart", retractor ribbon or malleable retractor, and the like. A blade surgical retractor include two or blades/blade mechanisms perpendicular or parallel to one another. A "camera cut-out," as used herein, is passageway indented into a blade. Camera cut-out 808 may allow for the insertion of stereoscopic camera module 400 along the length of blade 804. Stopper 812 may be embedded at one end of blade 804 along the width of the camera cut-out 808 to prevent stereoscopic camera module 400 from passing the edge of blade 804 and secretion the position. A "stopper," as used herein, is a device used to hold an item in place. Stopper 812 may include material such as rubber, plastic, foam, and the like.

Figure 9A:
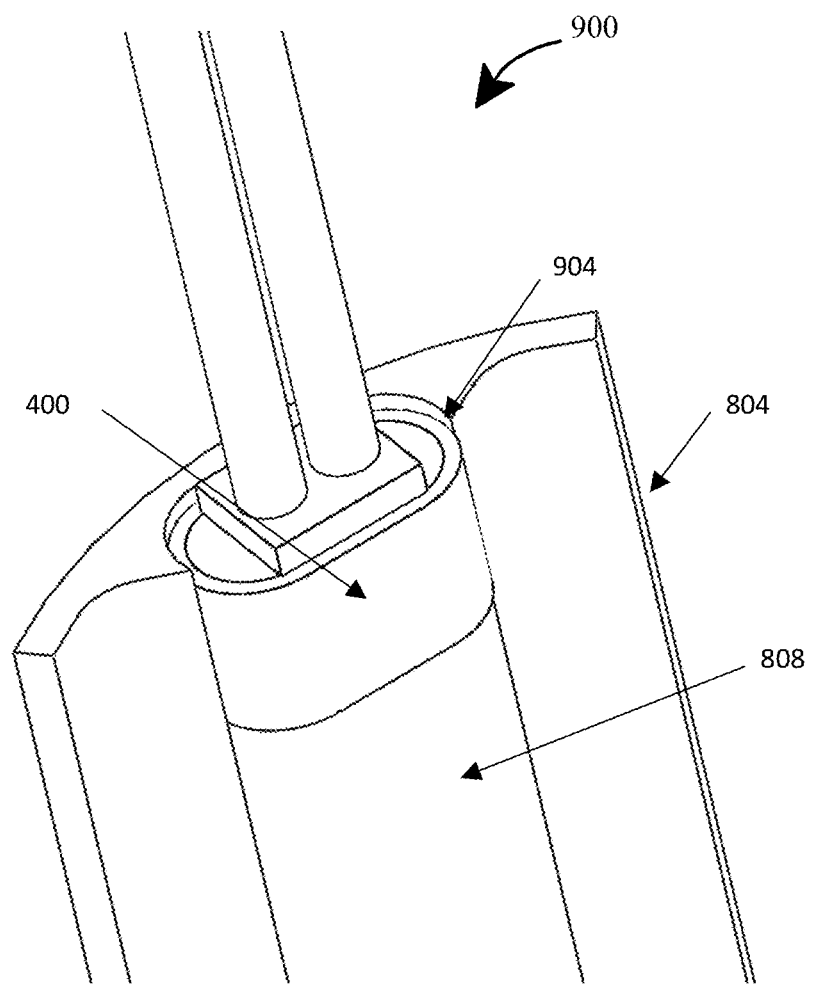
FIG. 9A illustrates a stereoscopic camera module being inserted into a camera cut-out and being forcibly maintained within the channel of the camera cut-out 808 via a retaining wall.

Referring now to FIG. 9A, an exemplary diagram a stereoscopic camera module 400 being inserted into a camera cut-out 808 is illustrated. The stereoscopic camera module 400 may be forcibly maintained within the channel of the camera cut-out 808 via a retaining wall 904 of blade 804.

Figure 9B:
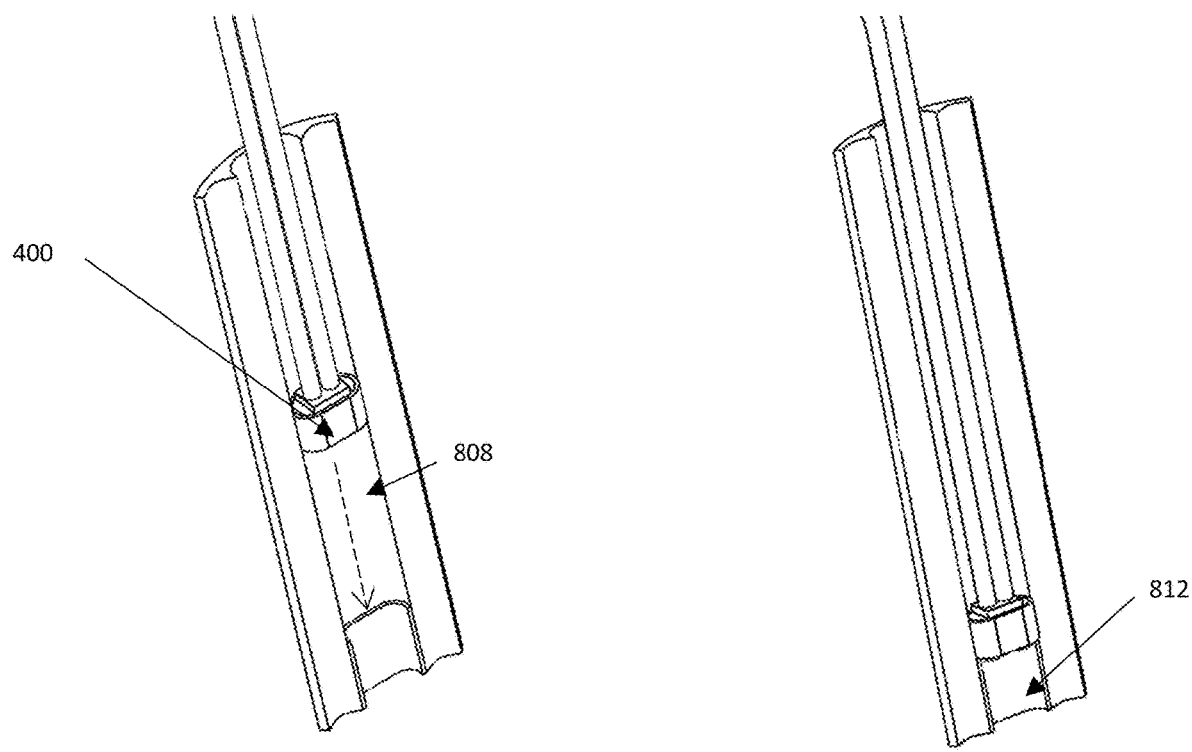
FIG. 9B illustrates a stereoscopic camera module traveling down a camera cut-out path until it comes into contact with a stopper.

Referring now to FIG. 9B, an exemplary diagram of stereoscopic camera module 400 traveling down a camera cut-out 808 path until stereoscopic camera module 400 comes into contact with a stopper 812 is illustrated.

Figure 9C:
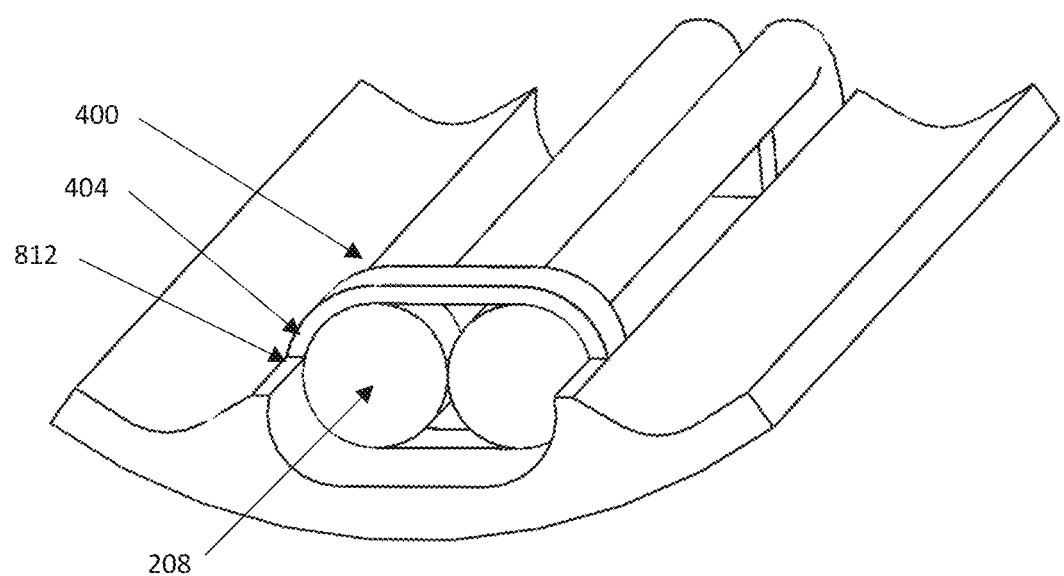
FIG. 9C illustrates a perspective-bottom view of a stereoscopic camera module that come into contact with a stopper, where the stopper may have a wall thickness no greater than the thickness of the camera adapter housing so that the lenses have unobstructed view into the area below the blade mechanism.

Referring now to FIG. 9C, an exemplary perspective-bottom view is shown of a stereoscopic camera module 400 that is in contact with a stopper 812. Stopper 812 may have a wall thickness no greater than the thickness of the camera adapter housing 404 so that the lenses 208 have an unobstructed view into the area below the blade mechanism 800.

Figure 10:
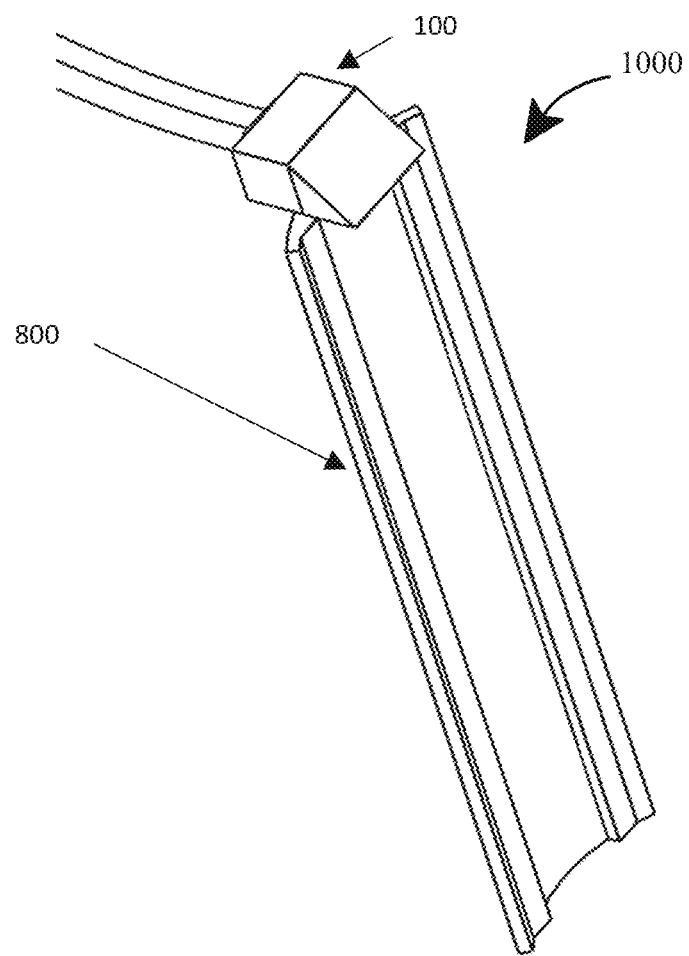
FIG. 10 illustrates a stereoscopic camera adapter that is attached to a blade mechanism.

Referring now to FIG. 10, an exemplary embodiment of stereoscopic camera adapter 100 attached to a blade mechanism 800 is illustrated. Embodiment 800 highlights the attachability of stereoscopic camera adapter 100 to a surgical device. In this embodiment, camera adapter 100 may include camera module 400, as described above, to capture image data.

Figure 11:
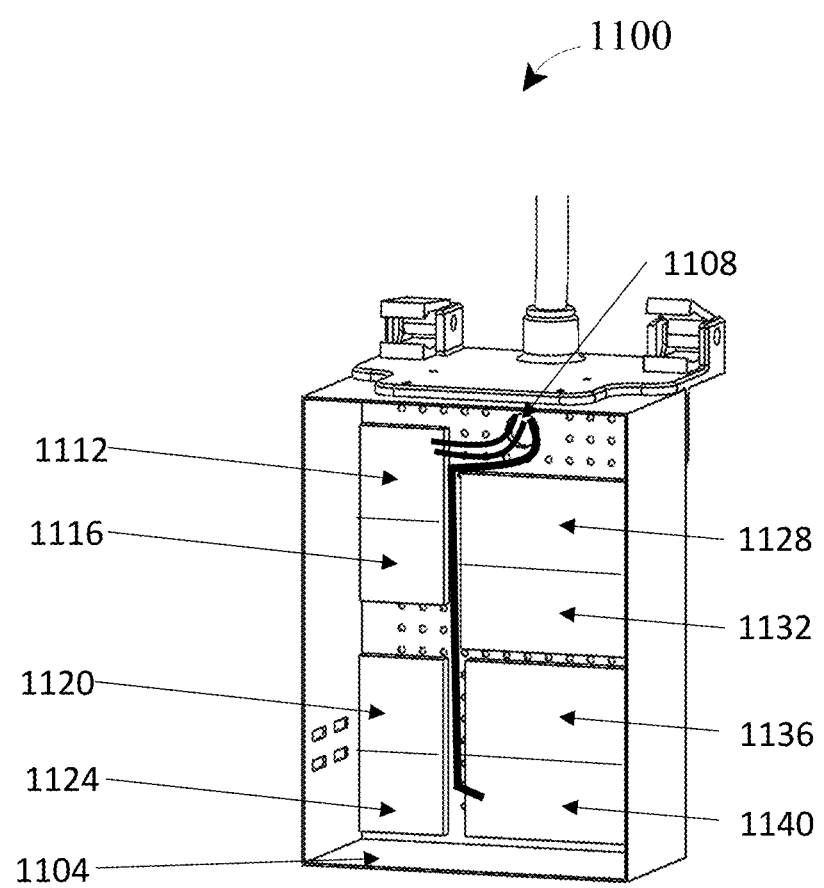
FIG. 11 illustrates an exemplary embodiment of an electronics module.

Referring now to FIG. 11 a partial view of the interior of an electronics module 1100 that enables receipt, processing, and transmission of stereoscopic video data is illustrated. "Stereoscopic video," as used herein, is a video that creates the illusion of depth for a viewer by way of binocular vision. Stereoscopic video data may include a video supplying the illusion of depth by the presentation of a slightly different image to each eye. "Stereoscopic video data," for the purposes of this disclosure, is data for a stereoscopic video. For example, image data captured by stereoscopic camera adapter 100 and may be used to produce a live feed video display of a person's anatomy to a surgeon during surgery. Electronics module 1100 includes a processor. Processor may include, without limitation, any processor described in this disclosure. Processor may be included in a computing device. Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting Computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device may include but is not limited to, for example, a computing device or cluster of computing devices in a first location and a second computing device or cluster of computing devices in a second location. Computing device may include one or more computing devices dedicated to data storage, security, distribution of traffic for load balancing, and the like. Computing device may distribute one or more computing tasks as described below across a plurality of computing devices of computing device, which may operate in parallel, in series, redundantly, or in any other manner used for distribution of tasks or memory between computing devices. Computing device may be implemented, as a non-limiting example, using a "shared nothing" architecture.

With continued reference to FIG. 11, computing device may be designed and/or configured to perform any method, method step, or sequence of method steps in any embodiment described in this disclosure, in any order and with any degree of repetition. For instance, computing device may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 11, electronics module 1100 may include an outer casing 1104 that encapsulates the interior electronics and acts as a barrier against external elements. The outer casing 1104 may be made of a metal, plastic, ceramic, or composite thereof. Inside the electronics module 1100 may be a central processing unit 1112, a graphics processing unit 1116, a random-access memory 1120, a storage (e.g. solid-state drive) 1124, a wireless card 1112, a Bluetooth chip 1132, power module 1136, and light source 1140. Image data cables, including first image data cable 108A and second image data cable 108B, may pass through an outer casing hole 1102, and connect to the central processing unit 1112. First image data cable 108A and second image data cable 108B may also connect to the graphics processing unit 1116. The images captured by the cameras and sent through first image data cable 108A and second image data cable 108B may be delivered to the central processing unit 1112 or graphics processing unit 1116 via analog, SDI, USB, HDMI, DP, Ethernet or other industry standard interface or protocol. Then, the central processing unit 1112 may send the image data to the graphics processing unit 1116, or the graphics processing unit 1116 can independently implement software code to manipulate or correct the images for display. The random-access memory 1120 may also work in tandem with the central processing unit 1112 and graphics processing unit 1116 to execute the software code and software functions. After the software code is implemented on the graphics processing unit 1116, the image data may be transmitted to one or more head-worn visualization systems 608. Additionally, the processed image data may also be sent back to the central processing unit 1112 for direct wired or wireless transmission via the wireless card 1128 or Bluetooth chip 1132 to a plurality of displays. The storage 1124 maintains the software operating system and can also store recorded stereoscopic video from first camera 204A and second camera 204B. The light source 1140 may include an LED, Xenon-bulb, or some other light power source, which then transmits either light or power via a light source power cable. Power may be generated by or delivered to power module 1136, which then delivers power to the other electronics in the electronics module 1100. Power module may be linear, switched, or battery-based. Power module 1136 may include transistors and diodes, metal oxide semiconductor field-effect transistors (MOSFETs), insulated-gate bipolar transistors (IGBTs), silicon-controlled rectifiers (SCRs), and the like.

Still referring to FIG. 11, in some embodiments, electronics module 1100 may utilize cloud computing to optimize the processing and transmission of image data. "Cloud computing," as used herein, is the on-demand availability of computer system resources, such as data storage and computing power, without direct active management by a user. Cloud computing service may include servers, storage, databases, networking, software, analytics, and intelligence—over the Internet ("the cloud") to offer faster innovation, and flexible resources.

Figure 12:
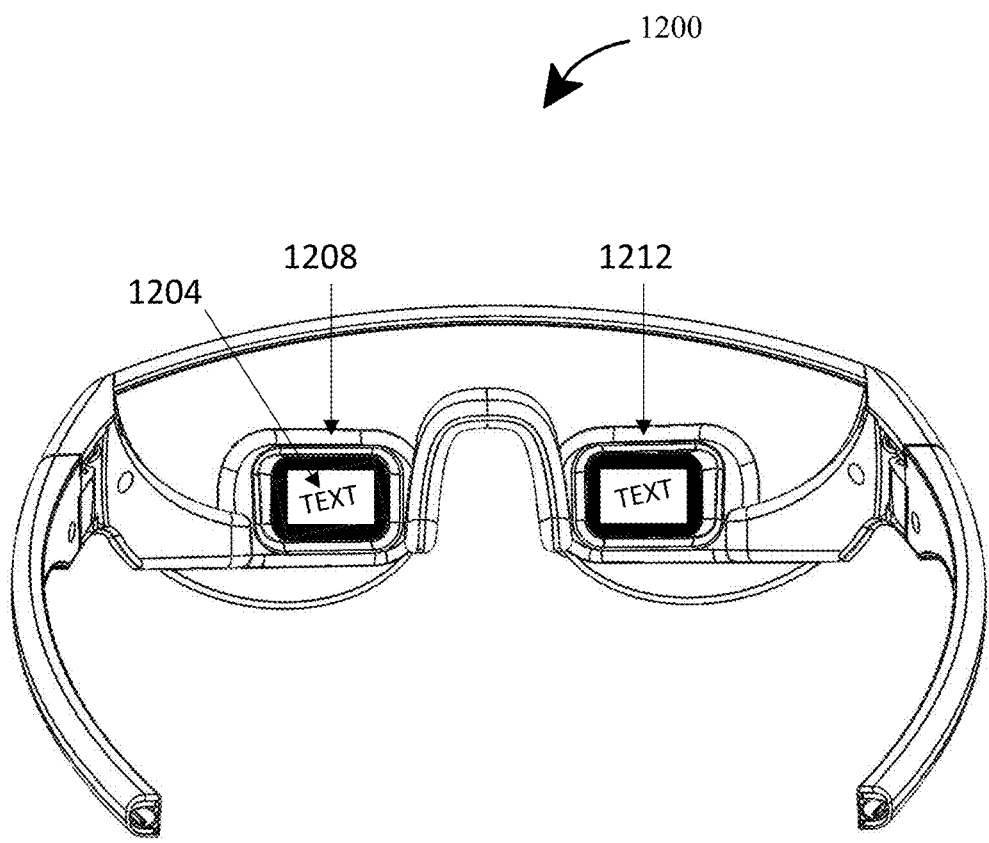
FIG. 12 illustrates an exemplary embodiment of a head-worn visualization system.

Referring now to FIG. 12, a head-worn visualization system 1200 displaying first camera 204A view of the TEXT label 1204 on a left display 1208 and the second camera 204B view of the TEXT label 1204 on a right display 1212 is illustrated. The left display 1208 and right display 1212 can be an organic light-emitting diode (OLED), a light-emitting diode (LED), a liquid-crystal display (LCD), a liquid-crystal on silicon display (LCoS), a projector, or any other type of pixel-based display. In some embodiments, head-worn visualization system 1200 may include a stereoscopic visualization portal system as disclosed in U.S. Nonprovisional patent application Ser. No. 15/607,035, filed on May 26, 2017, and titled "SYSTEM FOR STEREOSCOPIC VISUALIZATION ENABLING DEPTH PERCEPTION OF A SURGICAL FIELD," which is incorporated by reference herein in its entirety. In some embodiments, head-worn visualization system 1200 may include an interchangeable lens mechanism as disclosed in U.S. patent application Ser. No. 18/129,560, filed on Mar. 31, 2023, and titled "INTERCHANGEABLE LENS MECHANISM FOR A HEAD-WORN DISPLAY SYSTEM AND METHOD OF ASSEMBLING THE LENS MECHANISM," which is incorporated by reference herein in its entirety.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 13:
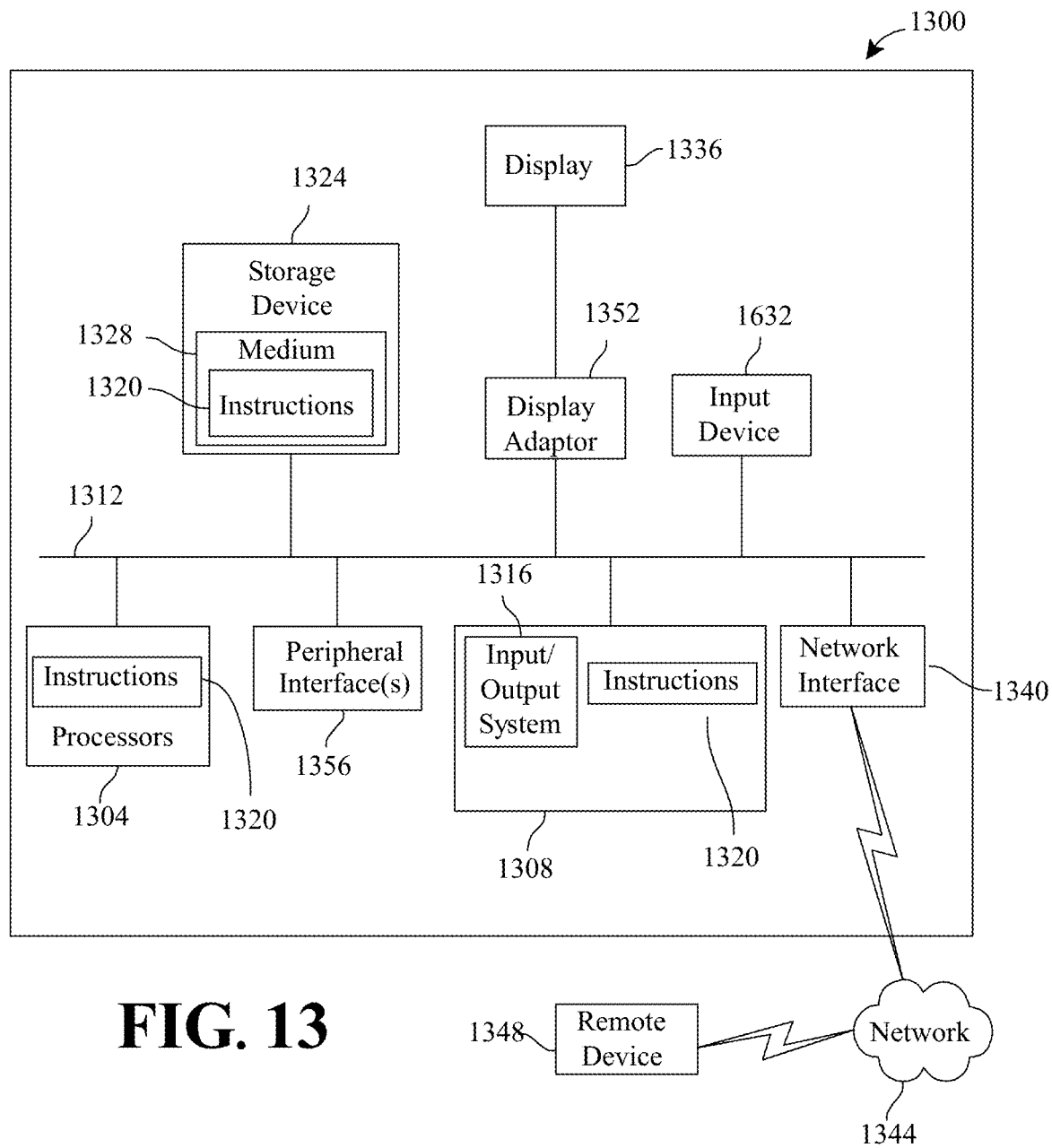
FIG. 13 is a block diagram of a computing system that can be used to implement any one or more of the methodologies disclosed herein and any one or more portions thereof.

FIG. 13 shows a diagrammatic representation of one embodiment of a computing device in the exemplary form of a computer system 1300 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1300 includes a processor 1304 and a memory 1308 that communicate with each other, and with other components, via a bus 1312. Bus 1312 may include any of several types of bus structures including, but not limited to, a memory bus, a memory controller, a peripheral bus, a local bus, and any combinations thereof, using any of a variety of bus architectures.

Processor 1304 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1304 may be organized according to Von Neumann and/or Harvard architecture as a non-limiting example. Processor 1304 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1308 may include various components (e.g., machine-readable media) including, but not limited to, a random-access memory component, a read only component, and any combinations thereof. In one example, a basic input/output system 1316 (BIOS), including basic routines that help to transfer information between elements within computer system 1300, such as during start-up, may be stored in memory 1308. Memory 1308 may also include (e.g., stored on one or more machine-readable media) instructions (e.g., software) 1320 embodying any one or more of the aspects and/or methodologies of the present disclosure. In another example, memory 1308 may further include any number of program modules including, but not limited to, an operating system, one or more application programs, other program modules, program data, and any combinations thereof.

Computer system 1300 may also include a storage device 1324. Examples of a storage device (e.g., storage device 1324) include, but are not limited to, a hard disk drive, a magnetic disk drive, an optical disc drive in combination with an optical medium, a solid-state memory device, and any combinations thereof. Storage device 1324 may be connected to bus 1312 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1324 (or one or more components thereof) may be removably interfaced with computer system 1300 (e.g., via an external port connector (not shown)). Particularly, storage device 1324 and an associated machine-readable medium 1328 may provide nonvolatile and/or volatile storage of machine-readable instructions, data structures, program modules, and/or other data for computer system 1300. In one example, software 1320 may reside, completely or partially, within machine-readable medium 1328. In another example, software 1320 may reside, completely or partially, within processor 1304.

Computer system 1300 may also include an input device 1332. In one example, a user of computer system 1300 may enter commands and/or other information into computer system 1300 via input device 1332. Examples of an input device 1332 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1332 may be interfaced to bus 1312 via any of a variety of interfaces (not shown) including, but not limited to, a serial interface, a parallel interface, a game port, a USB interface, a FIREWIRE interface, a direct interface to bus 1312, and any combinations thereof. Input device 1332 may include a touch screen interface that may be a part of or separate from display 1336, discussed further below. Input device 1332 may be utilized as a user selection device for selecting one or more graphical representations in a graphical interface as described above.

A user may also input commands and/or other information to computer system 1300 via storage device 1324 (e.g., a removable disk drive, a flash drive, etc.) and/or network interface device 1340. A network interface device, such as network interface device 1340, may be utilized for connecting computer system 1300 to one or more of a variety of networks, such as network 1344, and one or more remote devices 1348 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1344, may employ a wired and/or a wireless mode of communication. In general, any network topology may be used. Information (e.g., data, software 1320, etc.) may be communicated to and/or from computer system 1300 via network interface device 1340.

Computer system 1300 may further include a video display adapter 1352 for communicating a displayable image to a display device, such as display device 1336. Examples of a display device include, but are not limited to, a liquid crystal display (LCD), a cathode ray tube (CRT), a plasma display, a light emitting diode (LED) display, and any combinations thereof. Display adapter 1352 and display device 1336 may be utilized in combination with processor 1304 to provide graphical representations of aspects of the present disclosure. In addition to a display device, computer system 1300 may include one or more other peripheral output devices including, but not limited to, an audio speaker, a printer, and any combinations thereof. Such peripheral output devices may be connected to bus 1312 via a peripheral interface 1356. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, apparatuses, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A stereoscopic adapter for enabling down-hole data capture and transmission, the stereoscopic adapter comprising:
 a stereo camera module comprising: at least two cameras configured to collect stereoscopic video data that enables binocular vision; and
 a tubular retractor having a central channel therein that extends from top end to a bottom end of the retractor, the tubular retractor comprising an extended back wall cavity configured to receive therein the stereo camera module; the extended back wall cavity extending outwardly from the tubular retractor from the top end to a location between the top end and the bottom end and forms a cavity separate from the central channel, a bottom portion of the extended back wall cavity being sloped inwardly towards the central channel, the stereo camera module being sized to be inserted and removed from the back wall cavity and configured to engage the inwardly sloped bottom portion such that the at least two cameras are capable of being aimed into the central channel towards the bottom end of the tubular retractor.

2. The stereoscopic adapter of claim 1, further comprising an electronics module, wherein the stereo camera module is configured to capture and transmit image data to the electronics module.

3. The stereoscopic adapter of claim 2, wherein the electronics module is configured to transmit the image data to a head-worn visualization system.

4. The stereoscopic adapter of claim 1, wherein the stereo camera module further comprises an image signal processor board.

5. The stereoscopic adapter of claim 1, wherein the tubular retractor comprises a light guide, the light guide comprises a fiber optic cable.

6. The stereoscopic adapter of claim 1, wherein the stereo camera module is configured to be removably affixed to the bottom portion of the extended back wall cavity of the tubular retractor.

7. The stereoscopic adapter of claim 1, wherein the tubular retractor comprises a surgical retractor with a rotational stabilizing locking apparatus.

8. The stereoscopic adapter of claim 1, wherein the at least two cameras are aligned at an angle relative to one another for enabling increased parallax and stereopsis when capturing visible light.

9. The stereoscopic adapter of claim 1, wherein a light guide channel comprises a tubular passageway for guiding a supplementary instrument.

10. The stereoscopic adapter of claim 1, further comprising a fiber optic cable light guide.

11. The stereoscopic adapter of claim 1, further comprising a blade surgical retractor comprising a blade mechanism.

12. The stereoscopic adapter of claim 11, wherein a blade of the blade mechanism comprises a conical shape.

13. The stereoscopic adapter of claim 11, wherein a blade of the blade mechanism comprises a flat shape.

14. The stereoscopic adapter of claim 1, wherein a camera of the at least two cameras comprise a 3D camera.

15. The stereoscopic adapter of claim 1, further comprising a plurality of data cables connecting stereo camera module to an electronic module for the transmission of image data.

16. The stereoscopic adapter of claim 1, wherein the at least two cameras include lenses selected from the group of parfocal, varifocal, telescopic, superzoom, and/or wide-angle lenses.

17. A stereoscopic adapter configured to enable downhole data capture and transmission, the adapter comprising:
   a tubular retractor comprising an open interior channel extending from a top end to a bottom end of the tubular retractor, and an extended back wall cavity configured for insertion of a stereo camera module, the extended back wall cavity extending outwardly from the top end of the tubular retractor to form a cavity outside the tubular retractor in communication with the open interior channel of the tubular retractor, a bottom portion of the extended back wall cavity being sloped inwardly towards the open interior channel;
   the stereo camera module including at least two cameras configured to collect stereoscopic video data from a field of view at the bottom end of the open interior channel of the tubular retractor, the stereo camera module being sized to be removably inserted into the back wall cavity and, upon insertion configured to engage the inwardly sloping bottom portion such that the at least two cameras are capable of being aimed towards the field of view.

18. The stereoscopic adapter of claim 17, wherein the at least two cameras are aligned at an angle relative to one another to enable increased parallax and stereopsis when capturing visible light.

19. The stereoscopic adapter of claim 17, further comprising an electronics module, wherein the stereo camera module is configured to capture and transmit image data to the electronics module.

20. The stereoscopic adapter of claim 19, wherein the electronics module is configured to transmit the image data to a head-worn visualization system.

* * * * *